United States Patent [19]

Bright

[11] Patent Number: 4,492,688

[45] Date of Patent: Jan. 8, 1985

[54] ANTIBACTERIAL CYCLIC ETHERS OF 9-DEOXO-9A-AZA-9A-HOMOERYTHROMYCIN A AND INTERMEDIATES THEREFOR

[75] Inventor: Gene M. Bright, Groton, Conn.

[73] Assignee: Pfizer Inc., New York, N.Y.

[21] Appl. No.: 555,221

[22] Filed: Nov. 25, 1983

Related U.S. Application Data

[63] Continuation-in-part of Ser. No. 497,773, May 23, 1983, abandoned.

[51] Int. Cl.³ .................. A61K 31/71; C07H 17/08
[52] U.S. Cl. .................. 424/180; 536/7.2; 536/7.4
[58] Field of Search .......... 536/7.1, 7.2, 7.3, 7.4; 424/180

[56] References Cited

U.S. PATENT DOCUMENTS 3,417,077  12/1968  Murphy et al. ............ 536/7.2
4,328,334  5/1982   Kobrehel et al. .......... 424/180

FOREIGN PATENT DOCUMENTS 2094293  9/1982  United Kingdom ......... 536/7.2

*Primary Examiner*—Johnnie R. Brown
*Assistant Examiner*—Elli Peselev
*Attorney, Agent, or Firm*—Charles J. Knuth; Albert E. Frost; Peter C. Richardson

[57] ABSTRACT

Antibacterial 9,11-deoxo-11beta,9a-(epoxyalkano)9a-aza-9a-homoerythromycin A compounds, pharmaceutically acceptable salts thereof, pharmaceutical compositions comprising antibacterially-effective amounts thereof and a pharmaceutically acceptable carrier, the treatment of bacterial infections with antibacterially effective amounts thereof; and intermediates and processes therefor.

29 Claims, No Drawings

ANTIBACTERIAL CYCLIC ETHERS OF 9-DEOXO-9A-AZA-9A-HOMOERYTHROMYCIN A AND INTERMEDIATES THEREFOR

CROSS-REFERENCE TO RELATED APPLICATION

This application is a continuation-in-part of copending application Ser. No. 497,473, filed May 23, 1983, now abandoned.

BACKGROUND OF THE INVENTION

This invention relates to novel derivatives of 9-deoxo-9a-aza-9a-homoerythromycin A and of its 4"-epimer useful as antibacterial agents, to intermediates therefor, and to processes for preparation of said derivatives and said intermediates. More particularly it relates to cyclic ether derivatives of 9-deoxo-9a-aza-9a-homoerythromycin A and of its 4"-epimer, to pharmaceutically acceptable acid addition salts thereof and the use of said compounds as antibacterial agents, to intermediates therefor, and to processes for their preparation.

Erythromycin A is a macrolide antibiotic produced by fermentation and described in U.S. Pat. No. 2,653,899. Numerous derivatives of erythromycin A have been prepared in efforts to modify its biological and/or pharmacodynamic properties. Erythromycin A esters with mono- and dicarboxylic acids are reported in Antibiotics Annual, 1953-1954, Proc. Symposium Antibiotics (Washington, D.C.), pages 500-513 and 514-521, respectively. U.S. Pat. No. 3,417,077 describes the cyclic carbonate ester of erythromycin A, the reaction product of erythromycin A and ethylene carbonate, as an active antibacterial agent.

U.S. Pat. No. 4,328,334, issued May 4, 1982 describes 9-deoxo-9a-aza-9a-homoerythromycin A and refers to it by the name 11-aza-10-deoxo-10-dihydroerythromycin A. Since said compound is a ring expanded (homo) derivative of erythromycin A, nitrogen (aza) being the additional atom of the ring system, the nomenclature 9-deoxo-9a-aza-9a-homoerythromycin A is preferred for the parent ring system of the compounds of this invention.

Belgian Patent No. 892,357, published July 1, 1982, and its British counterpart, Application No. 2,094,293A, published Sept. 15, 1982, disclose the N-methyl derivative of 9-deoxo-9a-aza-9a-homoerythromycin A, as does my copending U.S. application Ser. No. 441,981, filed Nov. 15, 1982, which claims priority from U.S. application Ser. No. 399,401, filed July 19, 1982. The 4"-epimer of said N-methyl derivative is the subject of my copending U.S. application Ser. No. 441,979, filed Nov. 15, 1982. U.S. Pat. No. 4,382,085, issued May 3, 1983 describes 4"-epi erythromycin A; i.e., the 4"—OH group has the axial configuration. The 4"—OH in erythromycin A has the equatorial configuration.

SUMMARY OF THE INVENTION

It has now been found that certain cyclic ethers of 9-deoxo-9a-aza-9a-homoerythromycin A and of its 4"-epimer are effective antibacterial agents against Gram-positive and Gram-negative bacteria. The compounds have the formula (I)

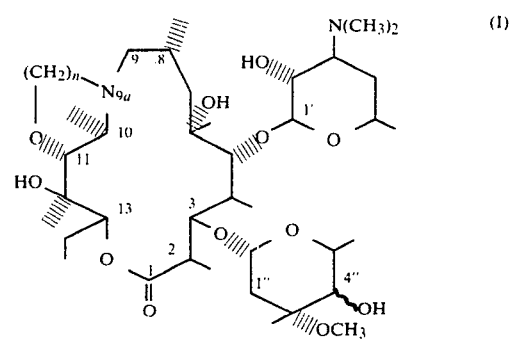

wherein n is 1, 2 or 3; and the wavy line at the 4"-position is generic to and embracive of both epimer forms, provided that when n is 1, the 4"-hydroxy group possesses the equatorial configuration. When n is 2 or 3, the epimeric forms of said compound differ structurally only in the configuration of the chiral center at the 4"-position; i.e., the 4"—OH group is either axial or equatorial. The axial configuration is represented by a solid or wedged shape line and the equatorial by a broken line of attachment of the OH group to the 4"-position. The terms "axial" and "equatorial" as used herein refer to the two possible chiral epimers at C—4" with respect to the 4"-hydroxyl and hydrogen.

Also included in this invention, and useful for the same purpose as formula (I) compounds, are the pharmaceutically acceptable acid addition salts thereof. Included among said slats, but by no means limited to said salts, are those enumerated below: hydrochloride, hydrobromide, sulfate, phosphate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and aspartate.

The present invention also embraces processes and intermediates useful for the preparation of compounds of formula (I). The intermediates are represented by formulae (II) and (III) below:

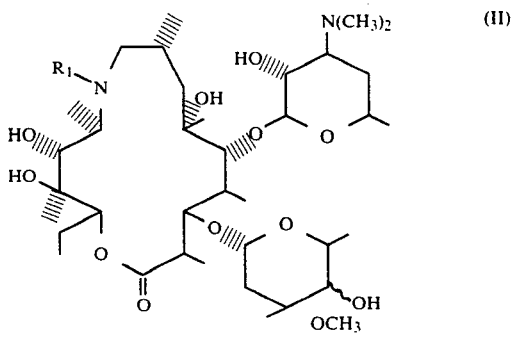

wherein $R_1$ is —$(CH_2)_p CN$ or —$(CH_2)_m$—$NH_2$; p is 1 or 2 and m is 2 or 3; and

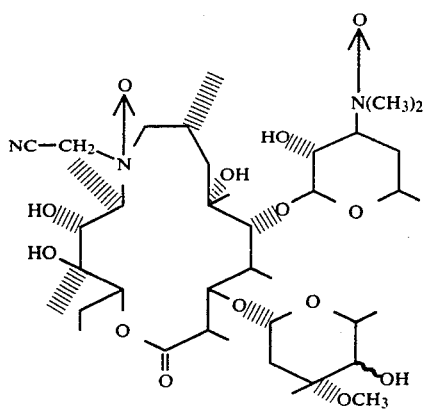

(III)

wherein the wavy line at the 4″-position of each of formulae II and III represents both epimers; i.e., the axial and equatorial configurations, at said position.

Also included in this invention are the compounds of formula (IV) which are formed as by-products in preparation of formula (I) compounds wherein n is 3:

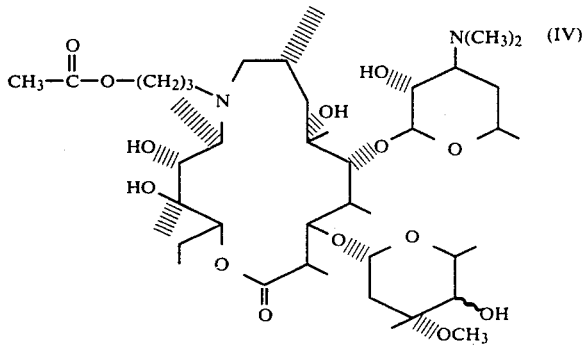

(IV)

wherein the wavy line at the 4″—OH group represents the axial and equatorial configurations at said position.

Compounds of formulae (I), (II) and (IV) and pharmaceutically acceptable acid addition salts thereof are effective antibacterial agents against Gram-positive microorganisms, e.g. *Staphylococcus aureus* and *Streptococcus pyogenes*, and against Gram-negative microorganisms, e.g. *Pasturella multocida* and *Neisseria sicca in vitro*. Additionally, compounds of formula (I) exhibit significant activity against *Neisseria gonorrhea* and Haemophilus in vitro and against many Gram-positive and Gram-negative microorganisms in vivo. In their oral anti-infective activity the formula (I) compounds are like 9-deoxo-9a-methyl-9a-aza-9a-homoerythromycin A, and quite unlike the corresponding 9a-desmethyl compound 9-deoxo-9a-aza-9a-homoerythromycin A which exhibits no practical oral activity in vivo.

DETAILED DESCRIPTION OF THE INVENTION

The compounds of formula (I) wherein n is 3 are prepared by cyanoethylation of the appropriate 9-deoxo-9a-aza-9a-homoerythromycin A epimers. An excess of acrylonitrile serves as both reactant and solvent. The reaction is generally carried out at the reflux temperature of the acrylonitrile solvent, about 77° C. until reaction is complete. Lower temperatures, e.g. 50° C. can be used but are avoided because of the longer reaction periods required. Higher temperatures can be used by using a solvent other than excess acrylonitrile and which is reaction-inert; i.e., does not enter into reaction with reactants and/or products so as to adversely affect the yield of the desired cyanoethyl derivative. A reaction-inert solvent can, of course, be used at whatever temperature the reaction is run. Suitable solvents are $C_{1-4}$ alcohols, ether (cyclic and acylic) such as dioxan, tetrahydrofuran, diethyl ether, diethylene glycol, dimethyl ether, aromatic hydrocarbons such as benzene, toluene and xylene. However, the preferred method comprises the use of excess acrylonitrile as solvent.

The progress of the reaction is monitored by thin layer chromatography (TLC) on silica gel plates and elution thereof with $CH_2Cl_2/CH_3OH$/concentrated $NH_4OH$ (6/1/0.1) and development of the plates with a spray of vanillin/ethanol/$H_3PO_4$ and heat.

The product is recovered by evaporation of the solvent as an off-white foam. It can be, and for convenience is, used directly in the next step of the process as is. TLC indicates the product is principally the desired monocyanoethylated product. Trace amounts of more polar products were detected on TLC.

The 9a-cyanoethyl derivative (II) thus produced is converted to the corresponding 9a-(gamma-aminopropyl) derivative (II) by means of hydrogenation over Raney nickel according to the procedure described herein. It is converted to the corresponding 7-membered ring cyclic ether by reaction of at least stoichiometric amounts of each of isoamyl nitrite and glacial acetic acid according to the procedure described herein. The compound of formula (IV), the corresponding 9a-(gamma-acetoxypropyl) derivative is produced as by-product.

The formula I compounds wherein n is 2 are prepared by alkylation of the appropriate 4″—OH epimer of 9-deoxo-9a-aza-9a-hydroxy-9a-homoerythromycin A 3′—N-oxide in a reaction-inert solvent with preferably an excess of bromoacetonitrile at from 20° C. to 100° C. and preferably at room temperature. Suitable solvents are chlorinated hydrocarbons such as methylene chloride, chloroform, aromatic hydrocarbons such as benzene, toluene, xylene, ethers such as diethylene glycol dimethyl ether, dioxan, tetrahydrofuran, diethyl ether.

The reaction is carried out in the presence of an acid acceptor, e.g. an organic base such as a $C_{1-4}$ trialkylamine, pyridine or an inorganic base such as an alkali metal carbonate or bicarbonate. The acid acceptor is used in equimolar proportion to the bromoacetonitrile which is generally used in excess to ensure optimum conversion of the macrolide reactant to product.

Catalytic hydrogenation of (III) over Pd/C in a reaction-inert solvent such as ethanol achieves removal of the 9a- and 3′-oxide groups to yield the cyanomethyl compound of formula (II) wherein p is 1.

The 9a-cyanomethyl derivative [formula (II)] thus produced is reduced to the corresponding 9a-(beta-aminoethyl) derivative (II) by means of sodium borohydride in the presence of cobaltous chloride in hydroxylic or non-hydroxylic solvents at room temperature. Molar ratios of $CoCl_2$ to $NaBH_4$ of about 1:5 are favored for this reduction. In practice an excess of $NaBH_4$ is used; e.g. up to 10 moles of $NaBH_4$ per mole of substrate. Reaction of the 9a-(beta-aminoethyl) derivative with at least stoichiometric amounts of each of isoamylnitrite/glacial acetic acid affords the corresponding 6-membered ring cyclic ether.

The 5-membered ring cyclic ether of formula I (n=1, 4"—OH=equatorial configuration) is prepared by reacting 9-deoxo-9a-aza-9a-homoerythromycin A with from 1-4 equivalents each of formaldehyde, conveniently as 37% aqueous solution, and formic acid, in a reaction-inert solvent, preferably at ambient temperature. Representative solvents are halogenated hydrocarbons such as methylene chloride, chloroform and carbon tetrachloride.

The critical feature of the reaction is the use of relatively low reaction temperature. The reaction is readily conducted from about 15° C. to 30° C., preferably from 20° C.–25° C. The reaction, if conducted at elevated temperatures, e.g. reflux temperature, affords the 9a-methyl derivative; i.e., reductive methylation occurs. At elevated temperatures, e.g. above about 50° C., methylation occurs exclusively. However, under the conditions of the present process cyclic ether formation occurs between the 11beta-OH and the 9a-aza groups.

Compounds of formulae (I), (III) and (IV) and of formula (II) wherein $R_1$ is —$(CH_2)_pCN$ wherein the 2' and/or 4"-hydroxy groups are acylated to give corresponding $C_{2-3}$ alkanoyl derivatives are conveniently prepared by standard acylation procedures such as those described by Jones et al., J. Med. Chem. 15, 631 (1972), and by Banaszek et al., Rocy. Chem. 43, 763 (1969). The 2'- and 4"-hydroxy groups are acylated by means of the appropriate acid anhydride [e.g. $(R_2CO)_2O$] in pyridine. Solvolysis of the 2',4"-ester with methanol produces the 4"-ester.

Formation of mixed esters, e.g. 2'-acetyl-4"-propionyl-, is readily achieved by acylating the 4"-ester ($R_3$=propionyl) with acetic anhydride in a reaction-inert solvent in the presence of potassium carbonate according to the procedure for mixed esters described by Jones et al. (loc, cit.).

Acid addition salts of the compounds of this invention are readily prepared by treating compounds having formulae I-IV with at least an equimolar amount of the appropriate acid in a reaction-inert solvent or, in the case of the hydrochloride salts, with pyridinium hydrochloride. Since more than one basic group is present in a compound of formula I or II, the addition of sufficient acid to satisfy each basic group permits formation of polyacid addition salts. When preparing acid addition salts of formulae I-IV compounds wherein the 2'—OH is acylated, isopropanol is used as solvent to avoid solvolysis of the alkanoyl group. The acid addition salts are recovered by filtration if they are insoluble in the reaction-inert solvent, by precipitation by addition of a non-solvent for the acid addition salt, or by evaporation of the solvent.

A variety of gram-positive microorganisms and certain gram-negative microorganisms, such as those of spherical or ellipsoidal shape (cocci), are susceptible to compounds of formulae (I), (II) and (IV). Their in vitro activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g. sick-room utensils; and as industrial antimicrobials, for example, in water treatment, slime control, paint and wood preservation.

For in vitro use, e.g. for topical application, it will often be convenient to compound the selected product by methods well known in the pharmacist's art into lotions, salves, ointments, creams, gels or the like. For such purposes, it will generally be acceptable to employ concentrations of active ingredient of from about 0.01 percent up to about 10 percent by weight based on total composition. The dosage form is applied at the site of infection ad libitum, generally at least once a day.

Additionally, formula (I) compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g. by subcutaneous or intramuscular injection, at a dosage of from about 1 mg/kg to about 200 mg/kg of body weight per day. The favored dosage range is from about 5 mg/kg to about 100 mg/kg of body weight per day and the preferred range from about 5 mg/kg to about 50 mg/kg of body weight per day. Vehicles suitable for parenteral injection may be either aqueous such as water, isotonic saline, isotonic dextrose, Ringer's solution or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the examples presented herein, no effort was made to recover the maximum amount of product produced or to optimize the yield of a given product. The Examples are merely illustrative of the process and of the products obtainable thereby.

In all examples, the terms "vanillin/ethanol/$H_3PO_4$ spray" and "vanillin/$H_3PO_4$ spray" refer to a solution of 1.0 g of vanillin, 100 ml of ethanol and 100 ml of $H_3PO_4$.

EXAMPLE 1

4''-Epi-9-deoxo-9a-(beta-cyanoethyl)-9a-aza-9a-homoerythromycin A

4''-Epi-9-deoxo-9a-aza-9a-homoerythromycin A (11.6 g, 15.8 mmole) was dissolved in 100 ml of acrylonitrile. The solution was refluxed for 19 hours, and then concentrated in vacuo, affording an ivory foam. Tlc inspection (silica gel plates; elution with $CH_2Cl_2/CH_3OH/$ concentrated $NH_4OH=6/1/0.1$; vanillin/$H_3PO_4$ spray with heat; $R_f=0.51$) revealed a single (less polar) dominant product with only trace amounts of (more polar) impurities. The crude product was used in the next step without further purification.

$^{13}$C-nmr [$CDCl_3$, $(CH_3)_4Si$ internal standard] ppm 177.92 (lactone>C=O), 118.86 (—C≡N), 102.49 (C—1'), 96.04 (C—1''), 40.25 [$(CH_3)_2N$—].

EXAMPLE 2

4''-Epi-9-deoxo-9a-(gamma-aminopropyl)-9a-aza-9a-homoerythromycin A

A solution of 12.8 g (16.2 mmoles) of 4''-epi-9-deoxo-9a-(beta-cyanoethyl)-9a-aza-9a-homoerythromycin A in 250 ml of absolute ethanol was combined with 12.8 g of Raney-Ni catalyst (50% water-wet) and hydrogenated on a Parr apparatus at 50 psi (3.52 kg/cm$^2$) for 19 hours. Tlc monitoring (silica gel plates; elution with $CHCl_3/CH_3OH$/concentrated $NH_4OH=6/1/0.1$; vanillin/$H_3PO_4$ spray with heat; $R_f=0.13$) showed complete reaction. The catalyst was filtered and the filtrate concentrated in vacuo to a foam. The crude product was dissolved in ca. 100 ml of methylene chloride. The solution was shaken with an equal volume of saturated aqueous sodium bicarbonate, the organic phase separated, dried with sodium sulfate, and concentrated in vacuo to an ivory foam (10.5 g). The entire sample was crystallized from warm ether, yielding 4.0 g, mp 135° C. (dec.).

$^{13}$C-nmr [($CDCl_3$, $(CH_3)_4$ internal standard] ppm 177.07 (lactone>C=O), 102.22 (C—1'), 95.77 (C—1''), 40.30 [$(CH_3)_2N$—].

EXAMPLE 3

4''-Epi-9,11-deoxo-11beta,9a-(epoxypropano)-9a-aza-9a-homoerythromycin A [Formula (I), n=3,4''-axial hydroxy] and 4''-Epi-9-deoxo-9-a-(gamma-acetoxypropyl)-9a-aza-9a-homoerythromycin A To a solution of 4''-epi-9-deoxo-9a-(gamma-aminopropyl)-9a-aza-9a-homoerythromycin A (3.37 g, 4.3 mmole) in 20 ml of chloroform, 574 mg (0.66 ml; 4.9 mmole) of isoamyl nitrite and 511 mg (8.52 mmole) of glacial acetic acid were added, and the mixture was vigorously refluxed for one hour. Tlc examination showed complete reaction and the presence of two major components (silica gel tlc plates momentarily immersed in a formamide/acetone solution and then air-dried; elution with $CHCl_3$/acetone=1/1; vanillin/$H_3PO_4$ spray with heat). The reaction mixture was shaken with 50 ml of 10% aqueous potassium carbonate. The organic phase was then separated, washed with 50 ml of saturated brine solution, dried over sodium sulfate, and concentrated in vacuo to a colorless foam (3.17 g).

Formamide-treated silica gel was prepared by adding 120 ml of formamide to a well-stirred 300 g silica gel (230-240 mesh)/600 ml acetone slurry; and then roto-evaporating solvent until a free-flowing powder was obtained. The crude product was chromatographed on 300 g of formamide-impregnated silica gel, eluting with $CHCl_3$/hexane=98/2 and monitoring collected fractions by tlc (utilizing the abovedescribed tlc system). Thus the two components produced in the reaction—the (less polar) title compound (344 mg, 10% yield), and 4''-epi-9-deoxo-9a-(gamma-acetoxypropyl)-9a-aza-9a-homoerythromycin A (400 mg; 11% yield)—were isolated as colorless amorphous solids.

In a second analogous run the chromatographed title compound (162 mg) was crystallized from acetone/water (yielding 94 mg, m.p. 139°-141° C.).

4''-Epi-9,11-deoxo-11beta,9a-(epoxypropano)-9a-aza-9a-homoerythromycin A: $^1$H-nmr ($CDCl_3$) delta 2.28 [6H, s, $(CH_3)_2N$—], 3.28 (3H, s, cladinose $CH_3O$—); $^{13}$C-nmr [$CDCl_3$, $(CH_3)_4Si$ internal standard] ppm 176.28 (lactone>C=O), 102.36 (C—1'), 96.18 (C—1''), 40.26 [$(CH_3)_2$—N—]; mass spectrum (m/e) 774 (molecular ion), 616.4, 599.4, 458,3, 442.3, 158.2, 127.1.

4''-Epi-9-deoxo-9a-(gamma-acetoxypropyl)-9a-aza-9a-homoerythromycin A: $^1$H-nmr ($CDCl_3$) delta 2.02

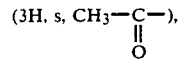

(3H, s, $CH_3$—C—),
           ‖
           O 2.27 [6H, s, $(CH_3)_2N$—], 3.28 (3H, s, cladinose $CH_3O$—).

EXAMPLE 4

9-deoxo-9a-(beta-cyanoethyl)-9a-aza-9a-homoerythromycin A 9-deoxo-9a-aza-9a-homoerythromycin A (1.0 g) was dissolved in 10.0 ml of acrylonitrile. The mixture was refluxed for 6 hours; then stirred overnight at ambient temperature. The mixture was then concentrated in vacuo to a tan foam. Chromatography of the crude product on silica gel (40 g; 70-230 mesh), eluting with a $CH_2Cl_2/CH_3OH$/concentrated $NH_4OH=10/1/0.01$ solvent mixture and monitoring fractions by tlc (silica gel plates; $CH_2Cl_2/CH_3OH$/concentrated $NH_4OH=6/1/0.1$ eluting system; vanillin/$H_3PO_4$ spray indicator with heat; $R_f=0.57$), afforded 605 mg (56% yield) of the title compound as a colorless foam.

$^1$H-nmr ($CDCl_3$) delta 2.34 [6H, s, $(CH_3)_2N$—], 3.33 (3H, s, cladinose $CH_3O$—); $^{13}$C-nmr [$CDCl_3$, $(CH_3)_4Si$ internal standard] ppm 177.62 (lactone>C=O), 118.85 (—C≡N), 103.01 (C—1'), 95.91 (C—1''), 40.33 [$(CH_3)_2N$—]. EXAMPLE 5

9-deoxo-9a-(gamma-aminopropyl)-9a-aza-9a-homoerythromycin A

A solution of 47 g (59.6 mmole) of 9-deoxo-9a-(beta-cyanoethyl)-9a-aza-9a-homoerythromycin A in 520 ml of ethanol was combined with 47 g of Raney-Ni catalyst (50% water-wet) and hydrogenated on a Parr apparatus at 50 psi for 2.75 hours. Tlc inspection (silica gel plates; elution with $CHCl_3/CH_3OH$/concentrated $NH_4OH=6/1/0.01$; vanillin/$H_3PO_4$ spray with heat) showed the reaction to be incomplete. The mixture was charged with 25 g of fresh catalyst, and hydrogenation at 50 psi (3.52 kg/cm$^2$) was continued for an additional 1.25 hours. The catalyst was filtered and the filtrate was concentrated in vacuo to a colorless foam. The crude product was dissolved in 600 ml of ethyl acetate. The solution was stirred with 800 ml of water and the pH was adjusted to 9.5 with 6N sodium hydroxide. The organic phase was dried over sodium sulfate and concentrated in vacuo to a foam. Chromatography on silica gel (800 g, 70–230 mesh) eluting with $CHCl_3/CH_3OH$/concentrated $NH_4OH=6/1/0.05$; $R_f=0.15$, afforded 14.7 g (31% yield) of the pure title compound as a colorless foam.

Crystallization of a 1.1 g sample from diethyl ether gave 545 mg of colorless crystals; mp 180°–183° C.

$^1H$-nmr ($CDCl_3$) delta 2.30 [6H, s, $(CH_3)_2N—$], 3.32 (3H, s, cladinose $CH_3O—$); $^{13}C$-nmr [$CDCl_3$, $(CH_3)_4Si$ internal standard] ppm 177.01 (lactone>C=O), 102.69 (C—1'), 95.27 (C—1"), 40.33 [$(CH_3)_2N—$].

EXAMPLE 6

9,11-Deoxo-11beta,9a-(epoxypropano)-9a-aza-9a-homoerythromycin A [Formula (I), n=3,4"-equatorial hydroxy] and
9-Deoxo-9a-(gamma-acetoxypropyl)-9a-aza-9a-homoerythromycin A To a solution of 9-deoxo-9a-(gamma-aminopropyl)-9a-aza-9a-homoerythromycin A (6.24 g, 7.90 mmoles) in 128 ml of chloroform, 1.01 g (1.16 ml; 8.63 mmoles) of isoamyl nitrite and 0.97 g (0.92 ml; 16.2 mmoles) of glacial acetic acid were added, and the mixture was vigorously refluxed for one hour. The mixture was stirred with 150 ml of water, and the pH adjusted to 8.0 with saturated aqueous sodium bicarbonate. The organic phase was separated and washed with an equal volume of water, dried over sodium sulfate, and concentrated in vacuo to a yellow foam. Tlc examination showed two components in the crude product (silica gel plates momentarily immersed in a 15:85 formamide/acetone solution and then air-dried; elution with $CHCl_3$/acetone=1/1; vanillin/$H_3PO_4$ spray with heat).

Formamide-treated silica gel was prepared by adding 360 ml of formamide to a well-stirred 900 g silica gel (230–400 mesh)/1800 ml acetone slurry; and then rotoevaporating solvent until a free-flowing powder was obtained. The crude product (5.8 g) was chromatographed on the 900 g of formamide-impregnated silica gel, eluting first with 2 liters of $CHCl_3$/hexane=7/3; and then with 3 liters of $CHCl_3$/hexane=8/2. The 5 ml fractions collected were tlc inspected utilizing the system described above. Thus the two components produced in the reaction—the (less polar) title compound (0.79 g, 13% yield), and 9-deoxo-9a-(gamma-acetoxypropyl)-9a-aza-9a-homoerythromycin A (0.76 g, 12% yield)—were isolated as colorless amorphous solids.

9,11-Deoxo-11beta,9a-(epoxypropano)-9a-aza-9a-homoerythromycin A: $^1H$-nmr ($CDCl_3$) delta 2.30 [6H, s, $(CH_3)_2N—$], 3.33 (3H, s, cladinose $CH_3O—$); $^{13}C$-nmr ($CDCl_3$) ppm 176.3 (lactone>C=O), 103.2 (C—1'), 96.2 (C—1"), 40.4 [$(CH_3)_2N—$]; mass spectrum (m/e) 616, 599, 458, 442, 158, 127.

9-Deoxo-9a-(gamma-acetoxypropyl)-9a-aza-9a-homoerythromycin A: $^1H$-nmr ($CDCl_3$) delta 2.01

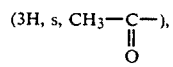

2.29

[3H, s, $(CH_3)_2—N—$], 3.31 (3H, s, cladinose $CH_3O—$); mass spectrum (m/e) 834.6.

EXAMPLE 7

9-Deoxo-9a-(cyanomethyl)-9a-aza-9a-homoerythromycin A 3',9a-bis-N-oxide

To a solution of 9-deoxo-9a-hydroxy-9a-aza-9a-homoerythromycin A 3'—N-oxide (11.0 g, 14.4 mmoles) in 138 ml of chloroform, 79 g (0.57 moles) of anhydrous potassium carbonate and 69 g (0.58 moles) of bromoacetonitrile were added. The mixture was stirred at ambient temperature for 5.25 hours. Tlc inspection [silica gel plates, elution with $CHCl_3/CH_3OH$/concentrated $NH_4OH=6/1/0.1$; vanillin/$H_3PO_4$ spray with heat] showed consumption of starting material and formation of a (less polar) product ($R_f=0.28$) with only trace amounts of impurities. The reaction was filtered and the filtrate was concentrated in vacuo to a viscous oil. The oil was stirred with 600 ml of diethyl ether—affording a colorless granular solid which was filtered and washed with 100 ml of ether prior to air-drying. The title compound thus obtained (10.4 g, 89.9% yield, of colorless granular solid) was used as is in the following Example.

EXAMPLE 8

9-Deoxo-9a-aza-9a-cyanomethyl-9a-homoerythromycin A

The title product of Example 7 (1.0 g), 10 ml of ethanol and 0.25 g of 5% Pd on carbon was charged into a 50 ml Parr flask and the flask repeatedly purged with nitrogen. It was then charged with hydrogen to 10 psi (0.70 kg/cm²) and hydrogenation carried out over a 4.5 hour period at room temperature. The reaction was removed from the flask, filtered and concentrated in vacuo to a foam. The foam was taken up in 100 ml of methylene chloride, 100 ml water added and the pH brought to 9.5 by addition of 6N NaOH. The methylene chloride layer was separated, dried ($Na_2SO_4$) and evaporated to dryness in vacuo to give 700 mg of a foam. Chromatography on silica gel (21 g, 70–230 mesh), and elution with $CH_2Cl_2$/MeOH/concentrated $NH_4OH$, 18/1/0.05 and evaporation of the eluate afforded the title product (135 mg).

$R_f$[silica gel plates, elution system $CHCl_3/CH_3OH$/concentrated $NH_4OH=6/1/0.1$; vanillin/$H_3PO_4$ spray with heat]=0.61.

$^1H$-nmr ($CDCl_3$) delta 2.26 [6H, s, $(CH_3)_2N—$], 3.28 (3H, s, cladinose $CH_3O—$); $^{13}C$-nmr [$CDCl_3$, $(CH_3)_4Si$ internal standard] ppm 178.0 (lactone>C=O), 116.76 (—C≡N), 102.78 (C—1'), 95.16 (C—1"), 40.30 [$(CH_3)_2N—$].

EXAMPLE 9

9-Deoxo-9a-(beta-aminoethyl)-9a-aza-9a-homoerythromycin A

Sodium borohydride (1.17 g, 0.0309 mole) was added to a mixture of 9-deoxo-9a-cyanomethyl-9a-aza-9a-homoerythromycin A (2.4 g, 3.1 mmoles), 72 ml of methanol and anhydrous cobaltous chloride (0.792 g, 6.1 mmoles) at room temperature. An exothermic reaction with much foaming occurred. The mixture was stirred at room temperature for two hours and was then concentrated under reduced pressure (aspirator) to a black oily residue. The residue was taken up in 50 ml of 1:1 water:methylene chloride solution, the pH adjusted to 2.5 by means of 1N HCl and the mixture stirred for ten minutes. The aqueous phase was separated, 25 ml of methylene chloride added and the pH adjusted to 9.5 by means of 1N NaOH. The organic phase was then separated, an equal volume of water added and the pH brought to 2.0 by addition of 1N HCl. Again the aqueous phase was separated, 25 ml methylene chloride added, and the pH raised to 9.5 by addition of 1N NaOH. The organic phase was separated, dried (Na$_2$SO$_4$) and concentrated under reduced pressure to a white foam (1.15 g) of crude title product.

Purification was accomplished by column chromatography of 1.05 g of crude product on 30 g of 70–230 mesh silica gel and elution with CHCl$_3$:CH$_3$OH:NH$_4$OH (6:1:0.1) and collection of 5 ml fractions. Fractions 80–150 contained the desired (more polar) material. They were combined and concentrated to small volume under reduced pressure. The concentrate was washed with saturated aqueous sodium bicarbonate solution, dried (Na$_2$SO$_4$) and evaporated in vacuo to a foam; 75 mg of title product.

EXAMPLE 10

9,11-Deoxo-11beta,9a-(epoxyethano)-9a-aza-9a-homoerythromycin A

[Formula (I), n=2,4"-equatorial hydroxy]

A mixture of 9-deoxo-9a-(beta-aminoethyl)-9a-aza-9a-homoerythromycin A (0.38 g, 0.488 mmole), chloroform (4 ml), isoamyl nitrite (0.072 ml, 0.536 mmole) and glacial acetic acid (0.056 ml, 0.976 mmole) was heated to reflux for one hour. The addition of isoamyl nitrite and glacial acetic acid was repeated and the mixture refluxed for two hours. It was cooled, added to a mixture of 10 ml chloroform and 15 ml of saturated aqueous sodium bicarbonate solution, and the pH adjusted to 9.5 by addition of 1N NaOH. The organic phase was separated, dried (Na$_2$SO$_4$) and concentrated at reduced pressure to give 0.37 g of a tan foam. Column chromatography on 55 g of formamide-treated silica gel (prepared as in Example 3) using chloroform:hexane (90:10) as eluting agent and collection of 5 ml fractions afforded the title product in fractions 81–130. The combined fractions were washed with water, dried (Na$_2$SO$_4$) and concentrated under reduced pressure to a white solid. The solid was taken up in methylene chloride, the solution filtered and evaporated in vacuo to give 26.5 mg of product as a white solid.

$^{13}$C-nmr [CDCl$_3$, chloroform internal standard] ppm 177.71 (lactone carbonyl), 103.36 (C—1'), 95.97 (C—1"), 40.40 [(CH$_3$)$_2$N—]; mass spectrum (m/e) 602, 444, 428.

EXAMPLE 11

9,11-Deoxo-11beta,9a-(epoxymethano)-9a-aza-9a-homoerythromycin A

[Formula (I), n=1,4"-equatorial hydroxy]

A solution consisting of 10.0 g (13.64 1 mmole) of 9-deoxo-9a-aza-9a-homoerythromycin A, 1.19 g (1.10 ml, 14.0 mmoles) of 37% aqueous formaldehyde, and 0.488 g (0.40 ml, 0.01 mole) of formic acid in 150 ml of chloroform was stirred at ambient temperature (ca. 25° C.) for 70 hours. Tlc inspection (silica gel plates; eluting with CH$_2$Cl$_2$/CH$_3$OH/concentrated NH$_4$OH=6:1:0.1; vanillin/H$_3$PO$_4$ spray with heat) showed a complex mixture of at least five components. The mixture was stirred with saturated aqueous sodium bicarbonate (400 ml), and the pH of the aqueous layer was adjusted to 9.5 with 6N sodium hydroxide. The organic phase was separated, dried over sodium sulfate, and concentrated in vacuo to a colorless foam. The crude product was chromatographed on silica gel (405 g; 70–230 mesh; eluting with CH$_2$Cl$_2$/CH$_3$OH/concentrated NH$_4$OH=12/1/0.05), thus affording 563 mg (5.5% yield) of the pure title compound as a colorless foam. R$_f$ (silica gel plates; CH$_2$Cl$_2$/CH$_3$OH/concentrated NH$_4$OH=6/1/0.1)=0.5.

$^{13}$C-nmr [CDCl$_3$, (CH$_3$)$_4$Si internal standard] ppm 173.37 (lactone>C=O), 103,48 (C—1'), 97.07 (C—1"), 83.31 (C—5), 81.01

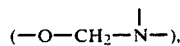

$(—O—CH_2—\overset{|}{N}—)$, 78.01, 76.11, 75.56, 40.24 [(CH$_3$)$_2$N—]; mass spectrum (m/e) 588, 571, 430, 414, 158, 127.

EXAMPLE 12

Following the procedures of Examples 7, 8 and 9, but using the appropriate starting materials, the compounds tabulated below are prepared.

| R$_1$ | 4"-OH |
|---|---|
| CH$_2$CN | axial and its 3', 9a-bis-N—oxide |
| CH$_2$CH$_2$NH$_2$ | axial |

EXAMPLE 13

Repetition of the procedure of Example 3 but using the 9a-beta-aminoethyl derivative of Example 12 as reactant affords the 6-membered ring ether derivative wherein the 4"—OH group has the axial configuration.

PREPARATION A

9-Deoxo-9a-aza-9a-hydroxy-9a-homoerythromycin A 3'—N-oxide

To a solution of 9-deoxo-9a-aza-9a-homoerythromycin A (10.0 g) in 40 ml of methanol, a total of 50 ml of 30% aqueous hydrogen peroxide was added dropwise while stirring over a 5–10 minute period. After stirring overnight at ambient temperature, the reaction mixture was poured onto a stirred slurry of ice (200 g), ethyl acetate (200 ml), and water (100 ml). Excess hydrogen peroxide was quenched by cautious dropwise addition of saturated aqueous sodium sulfite until a negative starch-iodine test was indicated. The layers were separated; and the aqueous layer was washed twice with 200 ml portions of ethyl acetate. The three organic extracts were combined, dried over anhydrous sodium sulfate, and evaporated to afford crude 9-deoxo-9a-aza-9a-hydroxy-9a-homoerythromycin A 3'—N-oxide as a colorless foam (8.6 g).

While the crude product proved satisfactory for use in the preparative procedure described below, purification was readily achieved by silica gel chromatography, eluting with a methylene chloride: methanol:concentrated ammonium hydroxide system (12:1:0.1). Progress of the column was followed by thin layer chromatography on silica gel plates using the system methylene chloride:methanol:concentrated ammonium hydroxide (9:1:0.1). The plates were developed with a vanillin spray [ethanol (50 ml): 85% $H_3PO_4$ (50 ml):vanillin (1.0 g)] indicator with heat. $^1$H-nmr (CDCl$_3$) delta 3.21

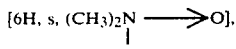

3.39 (3H, s, cladinose CH$_3$O—). MS: major peaks at m/e 576 (ion from desosamine fragmentation), 418 (aglycone ion-minus both sugars). Both peaks are diagnostic for

moiety within aglycone.

PREPARATION B

4"-Epi-erythromycin A Oxime

4"-Epi-erythromycin A (50 g, 0.0646 mole) was dissolved in 265 ml. pyridine. Hydroxylamine hydrochloride (112.2 g, 1.615 mole) was added and the slurry stirred 16 hours. The reaction mixture was stripped to a thick slurry, diluted with 300 ml isopropanol, stirred well and filtered with 3×100 ml isopropanol for wash. The filtrate and washes were combined, stripped to a water-soluble foam, and triturated with ether to yield crude title product as the hydrochloride salt (100 g). The latter was purified by distributing between CH$_2$Cl$_2$ and aqueous NaHCO$_3$ adjusted to pH 9.5 with dilute NaOH. The aqueous layer was separated and washed with ethyl acetate and then ether. All organic layers were combined, dried (Na$_2$SO$_4$) and stripped to yield title product as a white foam, 5.95 g; tlc R$_f$ 0.5 (60:10:1 CH$_2$Cl$_2$:CH$_3$OH: concentrated NH$_4$OH); $^1$H-nmr (CDCl$_3$) delta 2.31 [6H, s, (CH$_3$)$_2$N—], 3.32 (3H, s, cladinose CH$_3$O—).

PREPARATION C

4"-Epi-9a-aza-9a-homoerythromycin A

The title product of Preparation B (59.2 g, 0.0787 mole) was dissolved in 400 ml acetone. A slurry of NaHCO$_3$ (60 g) in 225 ml H$_2$O was added. Methanesulfonyl chloride (36.3 g, 24.5 ml) in 50 ml acetone was added portionwise over 10 minutes, while maintaining the temperature less than 30° by means of a cooling bath. The mixture was stirred 4.5 hours, stripped of acetone, CH$_2$Cl$_2$ (400 ml) added to the aqueous residue, and the pH adjusted to 5.6 with 6N HCl. The aqueous layer was separated, washed with two additional portions of CH$_2$Cl$_2$ and then adjusted to pH 9.5 with 6N NaOH. The basic solution was extracted 2×fresh CH$_2$Cl$_2$, 1×ethyl acetate and 1×ether. The basic organic extracts were combined, dried (Na$_2$SO$_4$) and stripped to yield title product as an ivory foam, 41 g; tlc R$_f$ 0.4 (60:10:1 CH$_2$Cl$_2$:CH$_3$OH: concentrated NH$_4$OH); $^1$H-nmr (CDCl$_3$) delta 2.27 [6H, s, (CH$_3$)$_2$N—], 3.29 (3H, s, cladinose CH$_3$O—); $^{13}$C-nmr [CDCl$_3$, (CH$_3$)$_4$Si internal standard] ppm 177.24 (lactone>C=O), 163.53 (amide>C=O), 102.29 and 95.24 (C—3, C—5), 40.22 [CH$_3$)$_2$N—].

PREPARATION D

4"-Epi-9-deoxo-9a-aza-9a-homoerythromycin A

The title product of Preparation C (40 g) was dissolved 600 ml CH$_3$OH. NaBH$_4$ (45 g) was added over 45 minutes maintaining temperature less than 38°. The reaction mixture was stirred 64 hours, then stripped to a thick slurry containing excess boro-hydride and boron ester complex of product. The latter was distributed between 500 ml each CH$_2$Cl$_2$ and H$_2$O, and the following sequence was repeated 3 times: The pH was adjusted with stirring to constant pH 2.5 with dilute HCl; the mixture was stirred vigorously 25 minutes; and the H$_2$O layer was separated, combined with 500 ml fresh CH$_2$Cl$_2$, adjusted to pH 9.5 with dilute NaOH and the CH$_2$Cl$_2$ layer separated. The pH 9.5 CH$_2$Cl$_2$ layer was combined with 500 ml fresh H$_2$O for repetition of the sequence. On the third pass, the pH 9.5 CH$_2$Cl$_2$ layer was dried (Na$_2$SO$_4$) and stripped to yield crude title product as a foam, 34 g, which was crystallized from 150 ml hot isopropyl ether, cooled and diluted with 300 ml of pentane, affording purified title product, 25.8 g; white crystals; tlc R$_f$ 0.5 (9:1 CHCl$_3$:diethylamine); R$_f$ 0.1 (90:10:1 CH$_2$Cl$_2$:CH$_3$OH: concentrated NH$_4$OH), mp 170°-180°; $^1$H-nmr (CDCl$_3$) delta 2.26 [6H, s, (CH$_3$)$_2$N—], 3.29 (3H, s, cladinose CH$_3$O—); $^{13}$C-nmr [CDCl$_3$, (CH$_3$)$_4$Si internal standard] ppm 179.44 (lactone>C=O), 103.57 and 96.70 (C—3, C—5); 41.50 [(CH$_3$)$_2$—N—].

PREPARATION E

4"-Epi-9-deoxo-9a-hydroxy-9a-aza-9a-homoerythromycin A 3'—N-Oxide

Stirring under N$_2$, title product of Preparation D (3.0 g) was dissolved in 15 ml of 1:1 THF:CH$_3$OH. Thirty percent H$_2$O$_2$ (5 ml) was added. After 0.5 hour, additional 30% H$_2$O$_2$ (2.5 ml) was added. After a further 0.5 hour, the reaction mixture was cautiously poured into 1:1 CH$_2$Cl$_2$:H$_2$O containing excess Na$_2$SO$_3$ (exothermic). The pH was 9. The aqueous layer was washed with fresh CH$_2$Cl$_2$ and then ethyl acetate. The organic layers were combined, dried (Na$_2$SO$_4$) and stripped to yield title product, 2.7 g, tlc R$_f$ 0.15 (60:10:1 CH$_2$Cl$_2$:CH$_3$OH:concentrated NH$_4$OH); $^1$H-nmr (CDCl$_3$) delta 3.21 [6H, s, (CH$_3$)$_2$N→O], 3.38 (3H, s, cladinose CH$_3$O—); MS: major peaks at m/e 576 (ion from desosamine fragmentation at C—5), 418 (N-hydroxyaglycone ion-minus both sugars). Both peaks diagnostic for —N—OH moiety with aglycone.

I claim:

1. A compound having the formula

15

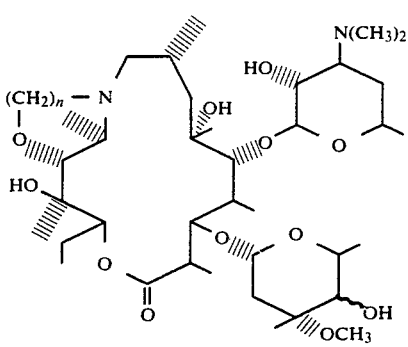

and the pharmaceutically acceptable acid addition salts thereof wherein n is 1, 2 or 3; the wavy line at the 4″—OH group represents the axial and equatorial configurations at said position; provided that when n is 1, the 4″—OH group has the equatorial configuration.

2. A compound according to claim 1 wherein n is 2.
3. The compound according to claim 2 wherein the 4″—OH group has the axial configuration.
4. The compound according to claim 2 wherein the 4″—OH group has the equatorial configuration.
5. A compound according to claim 1 wherein n is 3.
6. The compound according to claim 5 wherein the 4″—OH group has the axial configuration.
7. The compound according to claim 5 wherein the 4″—OH group has the equatorial configuration.
8. The compound according to claim 1 wherein n is 1.
9. A compound having the formula

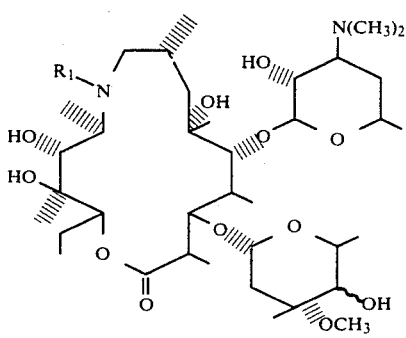

and the pharmaceutically acceptable acid addition salts thereof wherein $R_1$ is $(CH_2)_pCN$ or $-(CH_2)_m-NH_2$; p is 1 or 2; m is 2 or 3; and the wavy line at the 4″—OH group represents the axial and equatorial configurations at said position.

10. A compound according to claim 9 wherein $R_1$ is $(CH_2)_pCN$.
11. The compound according to claim 10 wherein p is 2 and the 4″—OH group has the axial configuration.
12. The compound according to claim 10 wherein p is 2 and the 4″—OH group has the equatorial configuration.
13. The compound according to claim 10 wherein p is 1 and the 4″—OH group has the axial configuration.
14. The compound according to claim 10 wherein p is 1 and the 4″—OH group has the equatorial configuration.
15. A compound according to claim 9 wherein $R_1$ is $-(CH_2)_m-NH_2$; and m is 3.

16. The compound according to claim 15 wherein the 4″—OH group has the equatorial configuration.
17. The compound according to claim 15 wherein the 4″—OH group has the axial configuration.
18. A compound according to claim 9 wherein $R_1$ is $-(CH_2)_m-NH_2$; and m is 2.
19. The compound according to claim 18 wherein the 4″—OH group has the axial configuration.
20. The compound according to claim 18 wherein the 4″—OH group has the equatorial configuration.
21. A compound having the formula

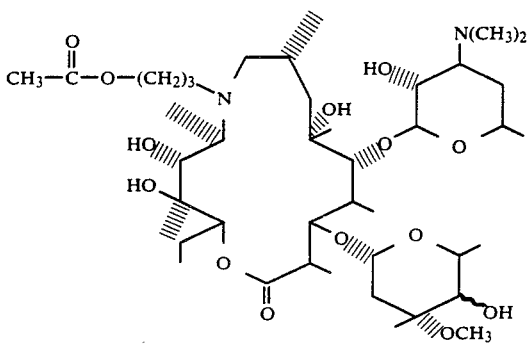

wherein the wavy line at the 4″—OH group represents the axial and equatorial configurations at said position.

22. A compound having the formula

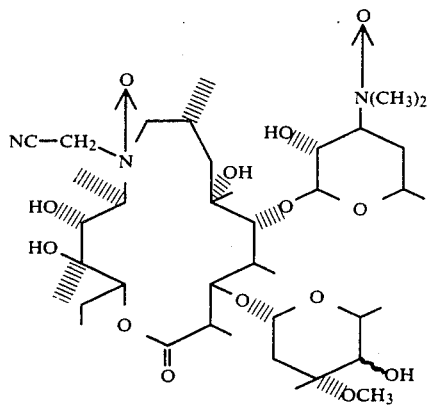

wherein the wavy line at the 4″-position represents the axial and equatorial configurations at said position.

23. The compound according to claim 22 wherein the 4″—OH group has the equatorial position.
24. The compound according to claim 22 wherein the 4″—OH group has the axial configuration.
25. A pharmaceutical composition comprising an antibacterial amount of a compound of claim 1 and a pharmaceutical carrier.
26. A method for treating a bacterial infection in a mammal which comprises administering to said mammal an antibacterially effective amount of a compound of claim 1.
27. A process for making a compound of formula (IA)

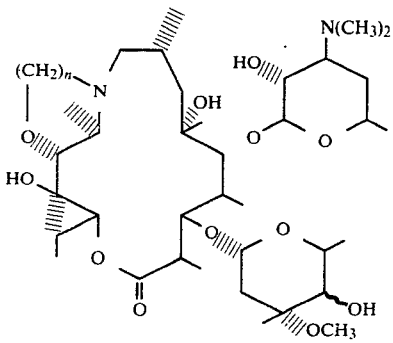

(IA)

wherein n is 2 or 3; the wavy line at the 4″—OH group represents the axial and equatorial configurations at said position; which comprises reacting a compound of the formula (II-A)

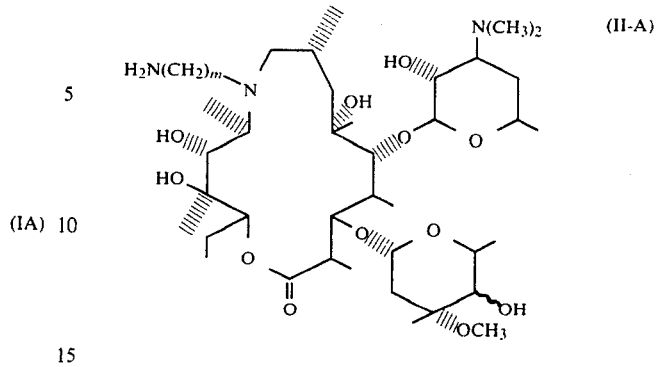

wherein m is 2 or 3 in chloroform with at least a stoichiometric amount of each of isoamyl nitrite and acetic acid.

28. A process for making a compound of formula (IB)

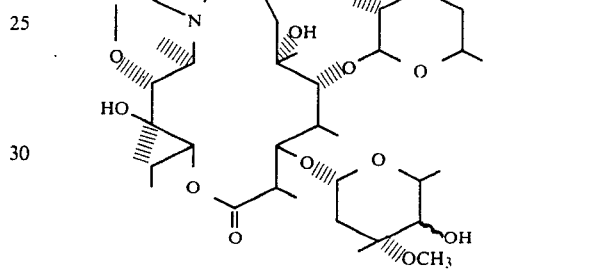

which comprises reacting 9-deoxo-9-aza-9-homoerythromycin A with formaldehyde and formic acid in a reaction-inert solvent at a temperature of from 15° C. to 30° C.

29. The process according to claim 28 wherein the solvent is chloroform.

* * * * *